United States Patent [19]

Fujimaki

[11] 4,421,683

[45] Dec. 20, 1983

[54] SUBSTANCE EFFECTIVE FOR PREVENTION OR THERAPY OF NEPHRITIS AND METHOD FOR PREPARATION THEREOF

[75] Inventor: Akira Fujimaki, Koganei, Japan

[73] Assignee: Zaidan Hojin Minsei Kagaku Kyokai, Tokyo, Japan

[21] Appl. No.: 328,534

[22] Filed: Dec. 8, 1981

[30] Foreign Application Priority Data

Dec. 15, 1980 [JP] Japan .................................. 55-176966
Dec. 15, 1980 [JP] Japan .................................. 55-176967

[51] Int. Cl.$^3$ ............................................... C07G 7/00
[52] U.S. Cl. ................................ 260/112 R; 424/177; 424/195
[58] Field of Search .................... 260/112 R; 424/177, 424/195

[56] References Cited

PUBLICATIONS

Chem. Abs. 82:53212v, 83:55188m, 92:210731q.

Primary Examiner—Allan Lieberman
Assistant Examiner—Patricia Short
Attorney, Agent, or Firm—Oblon, Fisher, Spivak, McClelland & Maier

[57] ABSTRACT

Glucopeptide in the form of a white powder, which is effective for prevention or treatment of nephritis, is produced by: preparing a concentrated extract from watermelon pulp juice; adding a lower alcohol to this extract to obtain an alcoholic solution with an alcohol concentration of approximately 80 to 95% by weight; adding acetone to the resulting solution in a volume of 1.5 to 2.5 times the volume of the solution to obtain a precipitate of glucopeptide; repeating at least once the purification procedure for the precipitate which comprises dissolution with a similar alcohol and precipitation from the resulting solution with acetone; and finally removing the remaining solvent to dryness.

9 Claims, 5 Drawing Figures

SUBSTANCE EFFECTIVE FOR PREVENTION OR THERAPY OF NEPHRITIS AND METHOD FOR PREPARATION THEREOF

BACKGROUND OF THE INVENTION

The present invention relates to the use of an extract from watermelons.

Watermelons have been known since long ago also in Japan to be effective for treatment with respect to diuresis and renal diseases. No reports, however, have been available on experiments both in animal tests and in analyses of the components of watermelons effective for renal diseases or diuresis. The inventor, with reference to the nephritis caused by heteronephrotoxic serum, namely Masugi nephritis (Matazo Masugi, Yasoichi Tomizuka: Journal of Society of Pathology of Japan, 21, 329, 1931), (Matazo Masugi: "Nephritis and other studies", Neiraku Shobo, Tokyo, Japan, 1948), using the second phase of Masugi nephritis, namely a system of combination of rabbits and ducks, has made studies on effective components in watermelons clinically and pathologically upon confirmation of 100% morbidity of nephritis, and found that a glucopeptide newly found in the edible portion of watermelons is effective and that the content of the glucopeptide is markedly reduced or is reduced even to zero depending on the species of the watermelon, the growing period of the watermelon, number of days after harvesting, and the treatment method. Therefore, it is not correct that any watermelon, no matter of what kind or freshness will do, as stated in the papers so far available.

BRIEF DESCRIPTION OF THE DRAWINGS

In the drawings, which indicate the characteristics of the purified glucopeptide obtained according to this invention.

SUMMARY OF THE INVENTION

Figure 1:
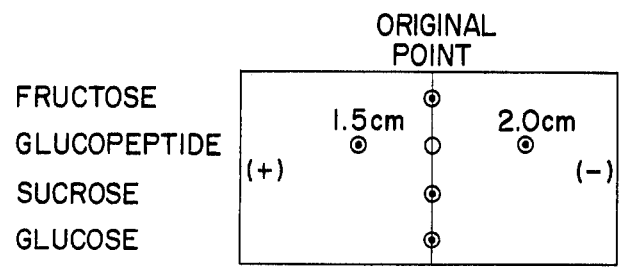
FIG. 1 is an illustration of the result of high-pressure paper electrophoresis indicating the presence of sugar.

The substance newly discovered by the present inventor is a glucopeptide, having unidentified sugar moiety and peptide moiety, exhibiting two different kinds of migration fractions in each of fractionations by high-pressure paper electrophoresis and thin-layer chromatography, indicating maximum absorption at 325 m$\mu$ by microbiurette analysis, showing a specific infrared absorption, having a specific rotation $[\alpha]_D^{25.5} = +374.91$ (water), and being, in chemical reactions, positive in each of Ninhydrin reaction, Glycyrrhizin reaction and reducing sugar reaction and negative in TCA (25%) reaction. The glucopeptide is hereinbelow called sometimes "the present substance".

That the present substance has remained undiscovered, in spite of being an effective substance contained in watermelon pulp juice useful for renal diseases or others as hereinafter described, is due to unknown essential properties thereof and also to the fact that no method for separation and purification thereof has hitherto been known. It can be said that the present invention has at last broken through these viels of obscurity.

The primary salient feature in the method adopted for obtaining the present substance resides in the finding that the above unknown substance can be obtained by a process which comprises adding a lower alcohol, preferably an alcohol having up to 4 carbon atoms, especially methanol or ethanol, to a concentrated extract prepared from an aqueous deproteinated solution of watermelon, preferably treated with activated charcoal, to prepared an alcoholic solution having an alcohol concentration of about 80 to 95%, adding acetone to the solution in a volume of about 1.5 to 2.5 times the volume of the alcoholic solution, and repeating at least once this procedure viz. solubilization-precipitation, to obtain a purified product of the present substance.

That is, in a 85% alcohol solution, proteins cannot be dissolved and thus removed, while glucopeptide can completely be dissolved therein. There are, however, impurities still dissolved in the solution such as free amino acids (including citrulline), glucides and inorganics, particularly potassium salts. By the addition of acetone in a volume twice the volume of the solution, only glucopeptide can be precipitated, while leaving the above impurities to remain dissolved in the solution. By repeating further at least once the alcohol-acetone treatment as described above, purification of glucopeptide can be accomplished.

It can be said that this treatment method is a novel method discovered for obtaining the present substance.

In this case, if the alcohol solution has an alcohol concentration less than 85%, particularly less than 80%, its capability of removing proteins will be insufficient. On the other hand, a concentration over 90%, particularly over 95%, is superfluous. The highest percentage of glucopeptide precipitated can be obtained when acetone is added in a volume twice the volume of the solution, and the precipitation percentage is lowered as the quantity is increased or decreased relative to this quantity, until the percentage is markedly lowered at a quantity of 1.5 or 2.5 times the volume of the solution.

The above concentrated extract of watermelon pulp juice is preferably prepared by carrying out at least twice the prepurification step, which comprises adding methanol or ethanol, with a concentration of, for example, 90% or higher, and subjecting resulting solution after removal of the precipitates formed to distillation under reduced pressure thereby to remove substantially the entire quantity of the alcohol and a partial quantity of water. The "watermelon pulp juice" which is the starting material in the prepurification step of the second or subsequent operation refers to the pulp juice after removal of substantially the entire quantity of the alcohol and a partial quantity of water from the product obtained in the preceding pre-purification step.

Another method of recovering purified glucopeptide according to the present invention comprises preparing an aqueous solution with a sugar content on the Brix scale of 2 to 20%, preferably 5 to 10%, from the concentrated extract of watermelon pulp juice which has been prepared in the manner as described above, adding to this aqueous solution glycyrrhizin preferably in an aqueous solution, particularly with a concentration of 10% or lower, at pH 3.5 or lower, preferably at pH 2.8 to 3.0, to obtain precipitates of a bound product of glycerrhizin and glucopeptide, subjecting the precipitates at least once to a purification step comprising dissolution of the precipitates in water of pH 5 to 6.5, preferably pH 5.8 to 6.0, and acidification of the solution formed to pH 3.5 or lower, preferably pH 2.8 to 3.0, to obtain a purified glycyrrhizin-glucopeptide conjugate or complex, dissolving the conjugate in a lower alcohol, preferably an alcohol having up to 4 carbon atoms, most preferably methanol or ethanol, adding acetone to the resultant solution to precipitate glucopeptide while leaving glycyrrhizin dissolved in the solution, and recovering the precipitated glucopeptide.

As a simpler method for the purpose of preparing a pharmaceutical for oral administration containing the concentrated effective substance of the invention together with some inorganics or other impurities instead of preparing a pure product by the purification steps comprising dissolution in alcohol and acetone precipitation or comprising formation of a conjugate or complex with glycyrrhizin and decomposition thereof as described hereinabove, it is also possible to prepare a solution of glucopeptide by adding a concentrated alcohol to a watermelon pulp juice to prepare a solution with an alcohol concentration of 80 to 95%, preferably 85 to 90%, exposing the solution to a temperature of room temperature (about 30° C.) or lower, preferably to a temperature not higher than about 0° C., and recovering the solution by removing the precipitates formed.

In this case, if the alcohol concentration is lower than 85%, particularly lower than 80%, proteins can be only insufficiently removed, and a concentration of 90% or higher, particularly 95% or higher, is uneconomical.

The treatment at lower temperatures is effective for removal by precipitation of potassium which is harmful to a patient suffering from nephritis, especially nephritis that requires chronic dialysis of the patient, and no satisfactory result can be expected at higher temperatures. The lower temperatures are not limited, but a temperature around 0° C. is practical.

DETAILED DESCRIPTION OF PREFERRED EMBODIMENTS

Examples for preparation of the present substance and, further, tests for investigation of the physical and chemical properties of the present substance together with test results of prevention and therapy of nephritis with the use of the present substance are described below.

EXAMPLE 1

The sugar content of a watermelon generally reaches a maximum after the cumulative sum of temperatures at noon of consecutive days, about 30 days, after flowering and fructification reaches 1000° C. This value is not constant but differs depending on factors such as the species of watermelon, the soil and the temperature. The pulp of a fresh watermelon weighing 2,380 g which has reached its highest sugar content is squeezed to obtain 1,100 ml of pulp juice. To this pulp juice, an equal volume of 99% ethanol or methanol is added to deactivate the enzymes, and the precipitated proteins and other components are removed by deposition or filtration to prepare a transparent 50% alcoholic solution.

This solution is then distilled under reduced pressure to produce a concentrated extract with a sugar content on the Brix scale of 70%. To this extract, again 99% ethanol or methanol is added. This step is followed by adjustment of the alcohol concentration to 85%, whereby the precipitations are again formed. The precipitates are removed by centrifugalization or filtration to obtain a transparent yellowish brown 85% alcoholic solution. This solution is again concentrated under reduced pressure to obtain a dark brown extract with a sugar content on the Brix scale of 80%. Pure water is added to this extract to prepare an aqueous solution with a sugar content on the Brix scale of 30 to 40%, which is in turn treated with an appropriate amount of activated charcoal to obtain a colorless transparent aqueous solution.

The adsorbed activated charcoal is eluted with an equal weight of hot water and the eluate is combined with the previous aqueous solution. Subsequently, the combined solution is adjusted to a sugar content on the Brix scale of 5 to 10%, and, while this solution is maintained at pH 2.8 to 3.0 by addition of hydrochloric acid thereto, an aqueous 5% glycyrrhizin solution is added thereto in an appropriate amount, whereby white glycyrrhizin-glucopeptide conjugate or complex is precipitated. The conjugate or complex is centrifuged to be separated into a white deposition and a colorless transparent supernatant. The presence or absence of glucopeptide in the aqueous solution can be determined by measurement of zero absorption in the ultraviolet region at 258 m$\mu$ of the supernatant (absorption of glycyrrhizin). The deposits are collected and pure water is added thereto. This step is followed by addition of NaOH to adjust the pH to 5.8–6.0, whereby the deposits are dissolved into a colorless transparent solution. On addition again of HCl to adjust pH 2.8–3.0, white glycyrrhizin-glucopeptide conjugate or complex is again precipitated, which is then similarly centrifuged to collect the deposits. This procedure is performed repeatedly to obtain a conjugate with high purity.

After the conjugate is dissolved similarly as described above by addition of pure water, the solution is subjected to freeze drying or vacuum drying to obtain 550 mg of powders of glycyrrhizin-glucopeptide conjugate. The bound ratio of glycyrrhizin to glucopeptide in the conjugate obtained is found to be 1:1, as determined from a calibration curve which has been determined from absorptions at 258 m$\mu$ in the ultraviolet region of aqueous solutions containing known weights of glycyrrhizin.

As the next step, 85% methanol is added to the white powders of the conjugate to prepare a solution, to which acetone in a quantity twice that of the volume of this solution is added, whereby glucopeptide is precipitated, while glycyrrhizin is left to be dissolved in the solution. The precipitate is filtered by a glass filter or other means, and the precipitate is washed with ether, chloroform, etc. to obtain a white glucopeptide. This glucopeptide is subjected to vacuum drying or once dissolved into an aqueous solution and thereafter subjected to freeze drying to produce 275 mg of white and slightly hygroscopic powders.

EXAMPLE 2

By squeezing 100 Kg of fresh watermelons (sugar content on the Brix scale: 8.58%, pH 5.77) as the result of planned cropping, 50 liters of pulp juice is obtained. To the juice is added 50 liters of 99% methanol to deactivate enzymes, and insolubles are removed by filtration. Then, by distillation under reduced pressure, methanol and other volatiles are evaporated to obtain 5 Kg of a dark brown extract with a sugar content on the Brix scale of 70%. The extract is diluted with 99% methanol to a methanol concentration of 85%, whereby the precipitates are again formed. The precipitates are deposited by leaving the mixture to stand overnight, and the supernatant is filtered off. The precipitates are removed by filtration or centrifugal deposition and the brown transparent 85% methanol solution is distilled under reduced pressure at 37° C. to obtain 4.7 Kg of a dark brown extract with a sugar content on the Brix scale of 70%. To the extract is added 5 liters of pure water and, after heating for a while, the extract is dissolved therein. The resultant solution is treated with an appropriate amount of activated charcoal to obtain a colorless transparent solution.

The used activated charcoal is mixed with an equal weight of hot water to elute a part of the adsorbed components, which is added to the previous aqueous solution. The combined solution is concentrated under reduced pressure at a temperature of 37° C. or lower to obtain 3.7 Kg of a slightly yellowish concentrated extract with a sugar content on the Brix scale of 70%. To the extract is added 99% methanol to prepare a pale yellow transparent methanol solution with a methanol concentration of 85%, to which acetone corresponding to twice the volume of the solution is gently added with stirring. As a result, a large quantity of white precipitates of the desired glucopeptide are formed, and the mixture is left to stand at a lower temperature.

After separation of the supernatant, the precipitates are again dissolved in 85% methanol, after which twice the volume of acetone is added similarly as described above to produce precipitates. This procedure is performed repeatedly, and the resulting precipitates are washed and subjected to vacuum drying or once dissolved in an appropriate amount of water and thereafter subjected to freeze drying. As a result, 12.5 g of white and slightly hygroscopic powders of glucopeptide are obtained.

The substance glucopeptide obtained according to the present invention has the physical and chemical properties as specified above, as shown by the following investigative tests.

(1) High-Pressure Paper Electrophoresis

Fractionation of the Present Substance into Sugar and Peptide (i) Sugar

Migration conditions:

2 KV, 1 hour, temperature: 4° C. (in n-hexane bath); filter paper: Whatman No. 1, 5×5.8 cm; buffer: 0.05 M borax solution (pH 9.2) containing 19.1 g/liter of borax ($Na_2B_4O_7.10H_2O$); detector: silver nitrate caustic soda solution.

Sample and results:

Aqueous solution containing 2% of the present substance; Control: each 1% aqueous solution of fructose, sucrose and glucose. The results are shown in FIG. 1, which shows that there are two fractionated migrations at 1.5 cm toward the anode and 2.0 cm toward the cathode side from the original point, both colored in black by silver nitrate, as contrasted to Control wherein there is no migration.

(ii) Peptide

Migration conditions:

3 KV, 1 hour; temperature: 4° C. (in n-hexane bath); filter paper: Whatman No. 1, 6×58 cm; buffer: formic acid, glacial acetic acid and water (5:15:80), pH 1.5; detector: 0.2% Ninhydrin ethanol solution.

Figure 2:
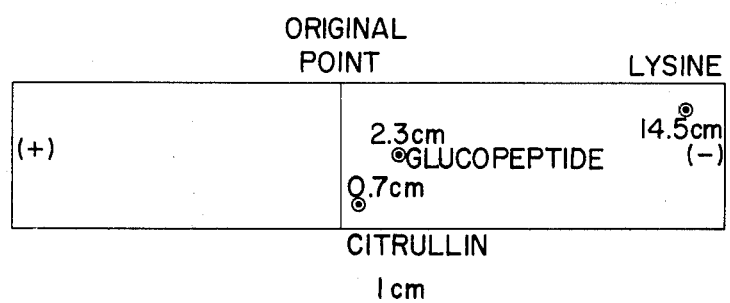
FIG. 2 is an illustration of the result of high-pressure paper electrophoresis indicating the presence of peptide.

Results:

As shown in FIG. 2, which shows that there is one migration of the present substance at 2.3 cm toward the anode side from the original point, clearly distinguished from Controls, i.e., citrulline migrated at 0.7 cm and lysine at 14.5 cm, all migrations being colored in blue violet by Ninhydrin.

(2) Thin-layer Chromatography

Figure 3:
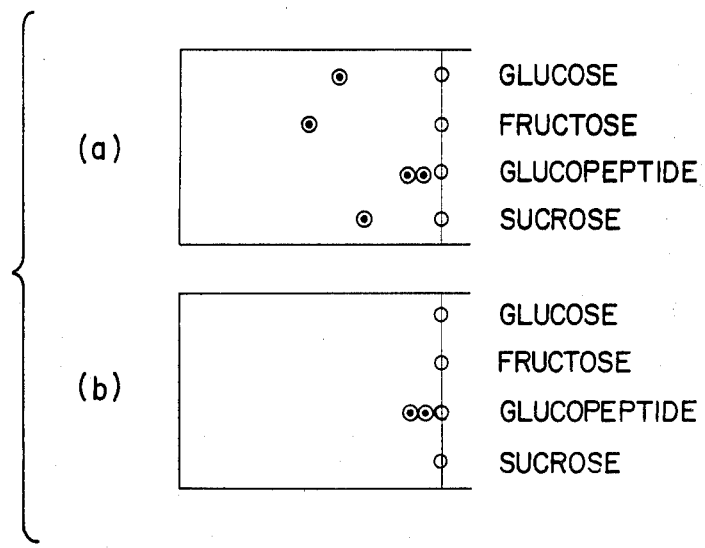
FIGS. 3a and 3b are illustrations of the result of thin-layer chromatography indicating respective fractions.

Adsorbent:

Avicel SF 0.25 mm, dried at 60°–80° C. for 20 minutes;

Developer:

ethyl acetate, pyridine, acetic acid and water (5:5:1:3);

Color former:

(i) silver nitrate solution in acetone (detection of sugar), (ii) 0.2% Ninhydrin solution in ethanol (detection of peptide);

Results:

as shown in FIG. 3, which indicates that there are two movable ratios different from the sugars of Control.

Figure 4:
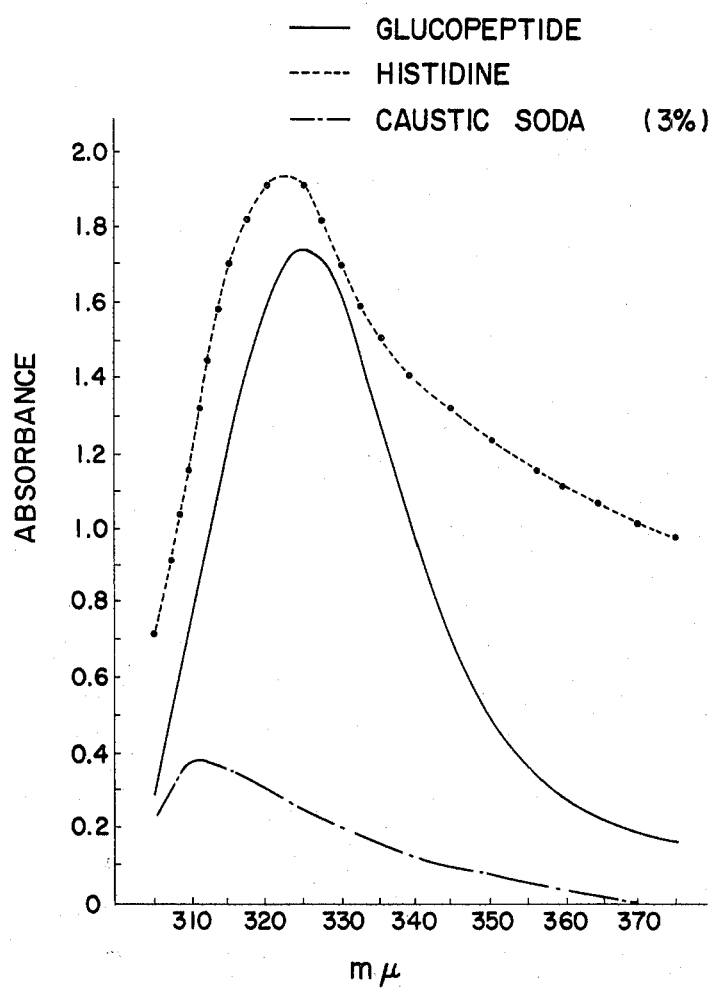
FIG. 4 is a graph indicating absorption by microbiurette analysis.

(3) Microbiurette Analysis 40 ml of 3% caustic soda solution containing 50 mg of the present substance is prepared, and orange color is indicated when 0.2 ml of the reagent according to this method is added. When the reagent is added to 50 mg of histidine similarly as above, blue color is indicated. By placing as blank 3% caustic soda, colorimetric quantitative determination is conducted after 15 minutes to obtain the results as shown in FIG. 4, indicating that the present substance and the histidine exhibit maximum absorption at 325 m$\mu$ and 322 m$\mu$, respectively. From these results, the present substance can be judged to be different from histidine.

(4) Measurement of Optical Rotation

The present substance exhibits an optical rotation of $[\alpha]_D^{25.5} = +374.91$ (water).

Figure 5:
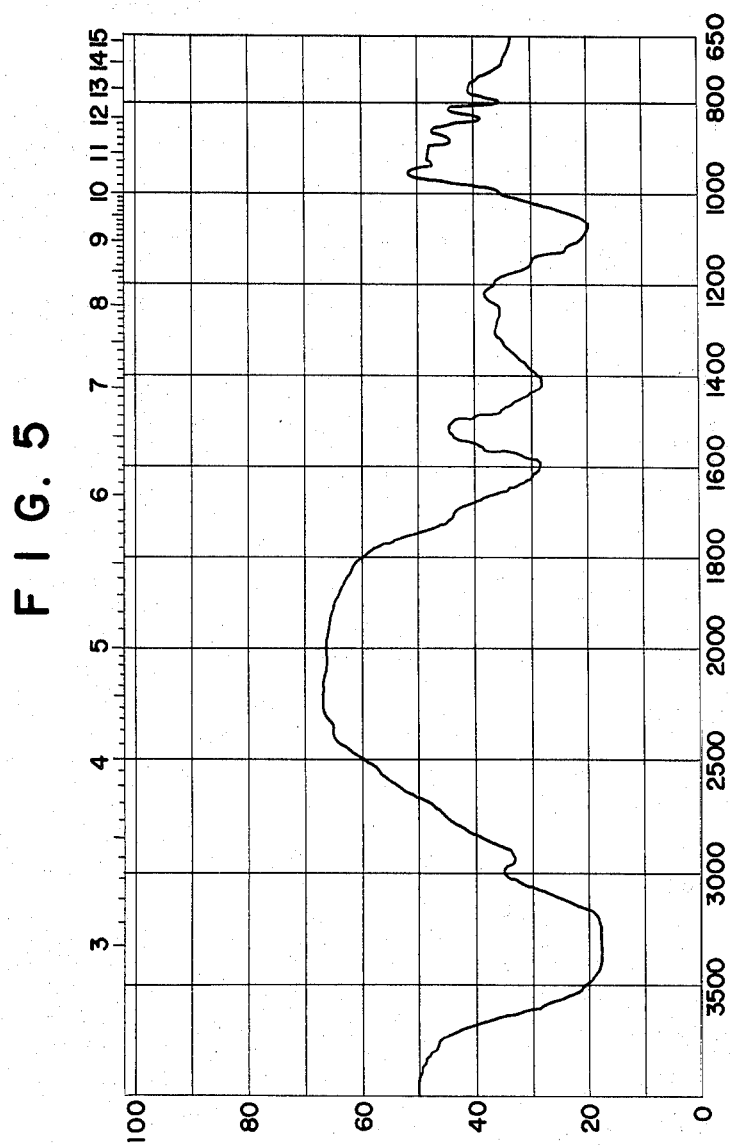
FIG. 5 is an infrared spectrum chart of the purified glucopeptide obtained according to the invention.

(5) Infrared absorption spectrum is specific as shown in FIG. 5.

Next, animal tests for showing that the present invention is effective for nephritis will now be described.

EXPERIMENTAL MATERIALS (a) Antigen

With reference to the method By Masugi et al, a 20% emulsion of rabbit kidney tissues is prepared.

(b) Duck antiserum against rabbit kidney

The above emulsion in a dose of 3 ml/Kg is injected intraperitoneally into a duck at intervals of 3 days. Then blood sampling is performed from the vein, and, after separation of serum, the antibody value is measured by the stratification method. After whole blood sampling, serum is separated therefrom.

(c) Antiserum injection

In recent years, Sphuler has reported that nephritis can be amply induced by only one antiserum injection, and hence the method of one injection is adopted in the present experiment.

(d) Medicaments employed

In test groups, watermelon peptide (present substance), citrulline, betamethasone and glycyrrhizin are employed, and isotonic sodium chloride solution in the control group.

EXPERIMENT METHOD

I. Morbidostatic Experiment

Twelve healthy male rabbits weighing 2.0-2.7 Kg are divided into 4 groups, three in each group, and 2.5 ml/Kg of antiserum with antibody value of 256 times is injected intravenously. This experiment is intended to test morbidostatic activity of each medicament, and each medicament is administered once prior to antiserum injection in each of the groups.

Test group:
Present substance:
  Intravenous injection of 10 mg/2 ml/body one hour before antiserum injection;
Citrulline:
  Intravenous injection of 10 mg/2 ml/body one hour before antiserum injection;
Betamethasone:
  Intramuscular injection of 1.2 mg/2 ml/body 6 hours before antiserum injection;
Control group:
  Isotonic sodium chloride solution is intravenously injected in a dose of 2 ml/body one hour before antiserum injection.

The observation term is 20 days, during which urine protein is measured by the sulfosalicyclic acid method. After completion of the observation, the animals are sacrificed by air embolism for pathological investigation of the kidneys.

II. Therapeutical Experiment

In this experiment, an antiserum with an antibody value of 512 times is employed. Six healthy male rabbits weighing around 2.5 Kg are divided into 3 groups, two per group, and 2.5 ml/Kg of antiserum is injected once intravenously. After 7-9 days, when noticeable urine proteins have appeared, the medicaments are administered as follows.

Present substance:
  Intravenous injection of 20 mg/2 ml/body;
Citrulline:
  Intravenous injection of 20 mg/2 ml/body; and
Betamethasone:
  Intramuscular injection of 1.2 mg/2 ml/body.

Observation is continued for 36 days, during which measurements of urine proteins and body weight are conducted every day. Necroscopy is conducted similarly as in the mobidostatic experiment.

Experimental Results

I. Morbidostatic Experiment (a) Clinical Observation

Present substance group:
In No. 1 and No. 2, there is no appearance of urine protein even on the 13th day, indicating inhibitory effect. In No. 3, appearance of protein is observed on the 12th day, but protein disappears on the 18th day when a double dose of 20 mg/2 ml/body is injected on the 15th day.

Bethamethasone group:
In all test animals, no appearance of urine protein is observed even to the 13th day, indicating inhibitory effect.

Citrulline group:
No. 8 is dead on the second day. In No. 7 and No. 9, protein appears on the 10th day. When a double dose of 20 mg/2 ml/body of the present substance is intravenously injected into No. 7, the protein disappears on the 16th day.

Isotonic sodium chloride solution group:
Protein appears on the 10th day in No. 10, and No. 11 on the 11th day, indicating no inhibitory effect.

(b) Necroscopy-pathologic Histological Investigation

Isotonic sodium chloride solution group:
Glomeruli exhibit very widely exudative tendency and increasing morbidity, differing individually in conditions and intensity within considerably wide ranges, but there is no difference between the right and the left kidneys. Changes of glomeruli from relatively slight morbid state to seriously morbid state may be as exemplified below.

(i) Manifesting lightly or moderately proliferation of cells of Mesangium or glomerulus fillet endothelium with no prominent fibrinoid exudation, not being accompanied as a whole by strong deformation of constitution of glomeruli, but micrangium being considerably blocked; and accompanied by exudation of leucocytes, etc.

(ii) Manifesting the aforesaid cell proliferation (hereinafter called M.E.P.) strongly unequally to invite fusion mutually between micrangiums, with prominent staining or irregularities in sizes of nucli, showing deformation in whole constitution; further manifesting adhesion partially with Bowman's endepidermis or showing fibrinoid exudation or swelling at a part of microangiums or a part of Mesangium.

(iii) Manifesting M.E.P. wholly or partially in one glomerulus by far stronger than the former (ii), generating even megakaryocte simultaneously with further intensified infiltration of fibrinoid or plasma components, with the constitution of glomerulus being for the most part lost as the increase of morbidity changes.

(iv) Manifesting a variety of disordered images at the stage of further progressed changes in appearance of glomeruli, such that most of glomeruli being occupied by exudates with Borman's endepidermis or M.E.P. cells being slightly observed therebetween; Bowman's endepidermis being not distinguishable from glomerulus, forming a mass of cells by proliferation of megakaryocytes as if it were a round small granulation node; exudation and proliferation existing instably mixed to fall widely in nucrosis; thus indicating anyway awful morbid changes. In the following test groups, in order to avoid repeated descriptions about the observations (i) to (iv) as mentioned above, they are only referred to in terms of the paragraph designations (i) through (iv).

Present substance group:
Glomeruli manifesting substantially no abnormal state, except for a very small number of glomeruli exhibiting slight congestion of fillet and very slight proliferation of microangium endothelium or Mesangium cells; being of course free from deformations of glomeruli, and glomerulus fillet being fibrous without mutual adhesion; thus indicating no exudative proliferative glomerulitis as mentioned with respect to the isotonic sodium chloride solution group.

But in case of No. 3, the changes in glomeruli are more rapid than in others, (i) and (ii) as described in the isotonic sodium chloride solution group slightly observed. That is, the observation of (ii) can be seen in 1 to 3 glomeruli as observed by 100 times field of vision.

Citrulline, glycyrrhizin groups:
Observations of glomeruli being substantially the same as in the isotonic sodium chloride solution group. That is, all of the observations (i) to (iv) can be seen.

Betamethasone group:
Observations of the glomeruli being substantially the same as in the present substance group. Accordingly, description is omitted.

II. Therapeutical Experiment

(a) Clinical Observation

Present substance group:
In No. 1, urine protein disappeared by injection for 9 days; in No. 2, urine protein disappeared by injection for 18 days.

Citrulline group:
In No. 3, no vanishing of urine protein observed by injection for 10 days, and therefore the dose of this substance changed to 20 mg/ml/body on the 11th day, whereby urine protein disappeared on the 10th day thereafter; No. 4 sacrificed on the 4th day.

Glycyrrhizin group:
In No. 5, No. 6, urine protein not disappeared by injection for 10 days; even after intramuscular injection of the medicament changed to betamethasone of 1.2 mg/ml/body for 14 days, no vanishing of urine protein achieved.

(b) Necroscopy-pathologic Histological Investigation

Present substance group:
While exhibiting slight differences between cases, as a whole including 6 to 7 healthy glomeruli, 7 to 8 of (i) and 2 to 4 of (ii) among about 17 glomeruli as observed by 100 times field of vision.

Of course, depending on cases, there are some devoid of (ii) and also those principally accompanied by (i). Generally speaking, exudation phenomenon is not prominent and swelling of fibrinoid is slight. Bowman's pouch is enlarged. Peripheral cell infiltration is slightly more prominent primarily on glomeruli which have suffered from changes. But, as compared with the isotonic sodium chloride solution group, the nephritis image is by far less serious. Thus, no further investigation of constituting elements other than glomerulus is necessary.

EXAMPLE 3

By squeezing pulp of 100 Kg of fresh watermelons, about 50 liter of juice (pH 5.77, sugar content on the Brix scale 8.58%) is obtained. To this water melon juice is added 50 liters of 99% alcohol to deactivate enzymes. Then, the precipitates are removed by filtration, centrifugal precipitation, etc. to obtain a transparent 50% methanolic solution. Subsequently, the solution is subjected to distillation under reduced pressure at 40° C. or lower to obtain a dark brown concentrated extract with sugar content of 70% to 80%. This extract is diluted with 99% methanol to a methanol concentration of 85% to 90%, whereby precipitates are again formed. The mixture is left to stand at a lower temperature (0° C.) overnight to cause deposition of the precipitates.

The supernatant is filtered off, and the deposits removed by filtration or centrifugation, to obtain a brown transparent 85 to 90% methanol solution. This methanol solution is distilled at 40° C. or lower to produce a concentrated extract. This extract is diluted with pure water to a sugar content on the Brix scale of around 30%, and the resulting solution is treated with an appropriate amount of activated charcoal to obtain a pale yellow aqueous solution. The activated charcoal is subjected to elution with hot water weighing twice as much as the charcoal. Both treated solutions are combined and admixed with ethanol for prevention of decay of the aqueous solution. As the next step, the dilute alcohol solution is distilled under reduced pressure at 40° C. or lower to obtain 2.7 Kg of a concentrated solution with sugar content of 80% (hereinafter referred to as present product).

By the practice of the procedures as described above, proteins, dyestuffs, potassium and others in watermelons can be removed. In particular, potassium is contained in watermelons in larger amounts than in foods in general, and for this reason consideration has been paid to make the product applicable for chronic dialysis patients under control of potassium intake. That is, while 1,400 mg of potassium is contained in 375 g of edible portion of watermelon with water content of 94%, the content of potassium is suppressed to less than 1/6 of this quantity by the use of the present method, as will be apparent from the results of flame analysis.

Next, 3 g of the present product is dissolved in 10 ml of pure water and administered three times per day in clinical experiments, including 12 cases of acute nephritis and 3 cases of chronic nephritis, 15 cases as a total, of which 9 cases are male and 6 cases female, aging from 22 to 54. From the clinical results, vanishing or improvement of edema and diuretic effect, namely increase of urine quantity and improvement of urine appearance, are observed upon administration of the present product, exhibiting 80% effectiveness. In all cases, no symptoms of side-effects whatsoever were observable.

The present product can be administered as an aqueous solution or as granules with the addition of four-fold quantity of lactose.

What is claimed is:

1. A method of preparing a substance effective for prevention or therapy of nephritis, which comprises preparing a concentrated extract from watermelon pulp juice, adding to the extract a lower alcohol to provide an alcoholic solution with an alcohol concentration of about 80 to 95% by weight, adding acetone to the resulting solution in a volume of 1.5 to 2.5 times the volume of said solution to obtain a precipitates of glucopeptide, further repeating at least once the purification procedure for the precipitate which comprises dissolution with a similar alcohol and precipitation from the resulting soluton with acetone, and finally removing the remaining solvent to dryness to obtain a white powder of glucopeptide.

2. A method according to claim 1, wherein the concentrated extract is prepared by performing a prepurification step at least twice, which step comprises adding an alcohol selected from the group consisting of methanol and ethanol to watermelon pulp juice, and subjecting the resulting solution after removal of the precipitates formed to distillation under reduced pressure thereby to remove substantially the entire quantity of the alcohol and a partial quantity of water, and at least one of said pre-purification steps is practiced so that the alcoholic solution will have an alcohol concentration of about 80 to 95% by weight.

3. A method according to claim 1, wherein the alcohol is selected from the group consisting of methanol and ethanol, the alcoholic solution has an alcohol concentration of about 85 to 90% by weight, and acetone is used in a volume of about twice the volume of the solution.

4. A method of preparing a substance effective for prevention or therapy of nephritis, which comprises preparing a concentrated extract from watermelon pulp juice, preparing an aqueous solution with a sugar content of 2 to 20% from said concentrated extract, adding glycyrrhizin to said aqueous soltuion at a pH of 3.5 or lower to obtain precipitates of a bound product of glycyrrhizin and glucopeptide, subjecting the precipitates at least once to a purification step which comprises dissolution of the precipitates in water of a pH of 5 to 6.5 and acidification of the solution formed to a pH of 3.5 or lower to obtain a purified glycyrrhizinglucopeptide conjugate, dissolving said conjugate in a lower alcohol, adding acetone to the resultant solution to precipitate glucopeptide while leaving glycyrrhizin dissolved in the solution, and recovering the precipitated glucopeptide.

5. A method according to claim 4, wherein the concentrated extract is prepared by performing a pre-purification step at least twice, which step comprises adding an alcohol selected from the group consisting of methanol and ethanol to watermelon pulp juice, and subjecting the resulting solution after removal of the precipitates formed to distillation under reduced pressure thereby to remove substantially the entire quantity of the alcohol and a partial quantity of water, and at least one of said pre-purification steps is practiced so that the alcoholic solution will have an alcohol concentration of about 80 to 95% by weight.

6. A method according to claim 4, wherein the alcohol is selected from the group consisting of methanol and ethanol; the alcoholic solution has an alcohol concentration of about 85 to 90% by weight; and acetone is used in a volume about twice the volume of the solution.

7. A method of preparing a substance effective for prevention or therapy of nephritis comprising glucopeptide as its principal ingredient, which method comprises adding a concentrated alcohol to watermelon pulp juice to prepare a solution with an alcohol concentration of 80 to 95%, subjecting the resulting solution to room temperature or lower temperature, and recovering the solution by removing the precipitates formed.

8. A method according to claim 7, wherein the alcohol concentration of the solution to be subjected to a lower temperature is 85 to 90% by weight and the temperature of room temperature or lower temperature is substantially not higher than 0° C.

9. A glucopeptide effective for nephritis, having unidentified sugar and peptide, exhibiting two different kinds of migration fractions in each of fractionations by high-pressure paper electrophoresis and thin-layer chromatography, indicating maximum absorption at 325 m$\mu$ by micro biurette analysis, showing a specific infrared absorption spectrum as shown in FIG. 5, having a specific rotation $[\alpha]_D^{25.5} = +374.91$ (water), and being in chemical reactions positive in each of Ninhydrin reaction, Glycyrrhizin reaction, and reducing sugar reaction and negative in TCA (25%) reaction.

* * * * *